United States Patent
Ishii et al.

(10) Patent No.: US 6,235,270 B1
(45) Date of Patent: May 22, 2001

(54) COSMETICS, SILICA-COATED METAL OXIDE POWDER AND PRODUCTION METHOD THEREFOR

(75) Inventors: Nobuaki Ishii; Koichi Wada; Kazuo Sekiguchi, all of Kawasaki; Michihiro Takama; Shinobu Ito, both of Tokyo; Kotaro Yano, Chiba; Yasuo Saito, Chichibu; Keiji Kawasaki, Chiba, all of (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/062,560

(22) Filed: Apr. 20, 1998

Related U.S. Application Data
(60) Provisional application No. 60/054,965, filed on Aug. 7, 1997, and provisional application No. 60/071,434, filed on Jan. 14, 1998.

(30) Foreign Application Priority Data

Apr. 18, 1997 (JP) .................................................... 9-101930
Nov. 20, 1997 (JP) .................................................... 9-334804

(51) Int. Cl.[7] ................................ A61K 7/42; A61K 7/00; C09C 1/62; C09C 1/36; C04B 14/04; C01G 23/047
(52) U.S. Cl. ........................... 424/59; 106/403; 106/414; 106/436; 106/491; 423/610; 424/60; 424/400; 424/401
(58) Field of Search ................................ 424/59, 60, 400, 424/401; 106/403, 414, 436, 491; 423/610

(56) References Cited

U.S. PATENT DOCUMENTS 4,375,373 * 3/1983 Abe et al. .............................. 106/308
5,643,557 * 7/1997 Eteve et al. .............................. 424/60

FOREIGN PATENT DOCUMENTS 0 581 651 A2    2/1994 (EP) .
8-104606    4/1996 (JP) .

\* cited by examiner

*Primary Examiner*—Shelley A. Dodson
(74) *Attorney, Agent, or Firm*—Sughrue, Mion, Zinn, Macpeak & Seas, PLLC

(57) ABSTRACT

Cosmetics comprising silica-coated metal oxide powder having a thickness of the silica coating of 0.1 to 100 nm, and a photocatalytic activity as measured by tetralin autooxidation method of 6 mmH$_2$O/min or less. Silica-coated metal oxide powder coated with a silica coating having an absorption peak intensity ratio I (I=I$_1$/I$_2$, wherein I$_1$ is an absorption peak intensity at 1,150 to 1,250 cm$^{-1}$ and I$_2$ is an absorption peak intensity at 1,000 to 1,100 cm$^{-1}$) between the infrared absorption spectra in the region of 1,150 to 1,250 cm$^{-1}$ and the region of 1,000 to 1,100 cm$^{-1}$ of 0.2 or more, and having a refractive index of 1.435 or more.

25 Claims, 2 Drawing Sheets

SiO₂/TiO₂(TS-K-1)

COSMETICS, SILICA-COATED METAL OXIDE POWDER AND PRODUCTION METHOD THEREFOR

DESCRIPTION OF RELATED APPLICATIONS

This application is based on and claims priorities of U.S. Provisional Application No. 60/054,965 filed on Aug. 7, 1997 and U.S. Provisional Application No. 60/071,434 filed on Jan. 14, 1998.

TECHNICAL FIELD OF THE INVENTION

The present invention relates to cosmetics, particularly cosmetics for ultraviolet shielding, and silica-coated metal oxide powder suitable for use therein and a process for producing the same. More specifically, the present invention relates to cosmetics giving excellent feeling during use of the cosmetics, having high ultraviolet shielding ability, and free of phototoxicity and excellent in storage stability, and relates to a silica-coated metal oxide powder having specific infrared absorption spectral peaks and having formed thereon a dense and practical silica coating. The silica-coated metal oxide powder of the present invention can be used for various ultraviolet-shielding materials, cosmetic materials, pigments and the like.

BACKGROUND ART

A cosmetic having ultraviolet shielding ability comprises an organic or inorganic material having ultraviolet shielding ability. The organic materials have a problem in safety due to degradability and, accordingly, inorganic materials are often being used at present. The inorganic material commonly used is a metal oxide. In particular, use of titania powder is widespread and zinc oxide powder is also used.

If titania is selected as an example, there are various titania powders with different particle sizes and it is known that ultraviolet shielding ability of titania powder depends greatly on its primary particle size.

A powder having a large primary particle size (about 200 nm) which is predominantly used as a pigment can exhibit good-shielding effect by scattering but it is not suitable for ultraviolet shielding cosmetics because the ultraviolet shielding ability is low. On the other hand, the fine powder (primary particle size: 10 to 30 nm) exhibits high ultraviolet shielding ability in the short wavelength region (UVB, wavelength: 290 to 320 nm) and can give feeling of transparency but has no shielding effect by the scattering and has a problem that the shielding effect against ultraviolet rays in the long wavelength region (UVA region; wavelength: 320 to 400 nm) is low. Further, titania powder having a primary particle size of about 100 nm can have a good shielding ability against ultraviolet rays in the long wavelength region (UVA), but the titania powder having such a particle size is low in spreadability and when it is incorporated into cosmetics, a problem arises that the feeling on use is uncomfortable.

In order to improve the feeling on use, an inorganic powder such as talc, mica or silica beads or an organic powder such as nylon or polystyrene is blended in some cases, however, these powders have no ultraviolet shielding ability and, on taking account of the ultraviolet shielding ability of cosmetics, the incorporating of these powders is limited.

The metal oxide such as titania and zinc oxide is known to have a photocatalytic activity effect and thus a possibility of adverse affect on the human body and for incorporating it into cosmetics, the metal oxide must be coated with an inorganic coating which is not degenerated by photocatalytic reaction. For this, various surface treated titania powders, for example, titania powders coated with a calcinated alumina coating, coated with a calcinated alumina coating combined with a further surface treatment by stearic acid, glycerol, etc., coated with a calcinated alumina and zirconium oxide coating coated with a calcined silica coating, and the like are commercially available. However, in conventional surface treated metal oxide powders, when incorporated in cosmetics, the coating has a poor effect of shielding photocatalytic activity, so that prevention of phototoxicity may be insufficient and degradation of organic components cannot be prevented. Furthermore, they have a fatal disadvantage in that the feeling, during use of the cosmetics, is not good since the properties of the coating are not appropriate.

The practical silica coating obtained through calcination in the normal sol-gel method generally has an absorption peak intensity ratio I ($I=I_1/I_2$, wherein $I_1$ is an absorption peak intensity at 1,150 to 1,250 $cm^{-1}$ and $I_2$ is an absorption peak intensity at 1,000 to 1,100 $cm^{-1}$) between the infrared absorption spectra in the region of 1,150 to 1,250 $cm^{-1}$ and the region of 1,000 to 1,100 $cm^{-1}$, of less than 0.2. This value I is known to have a tendency in general to become small after calcination. It is also known that due to the calcination, the chemical bond or functional group changes and the silica coating is altered in characteristics such as hydrophilicity or absorption ability of oil. On the other hand, the silica coating obtained without passing through calcination in the normal sol-gel method exhibits a some high absorption peak intensity in the region of from 1,150 to 1,250 $cm^{-1}$, however, the refractive index is less than 1.435 and the coating is low in density and is not practical. The density and the refractive index of the silica coating are generally considered to have a positive correlation (see, for example, C. JEFFEREY BRINKER, SOL-GEL SCIENCE, 581–583, ACADEMIC PRESS (1990)).

The first object of the present invention is to provide cosmetics giving excellent feeling on use, having high ultraviolet shielding ability, free of phototoxicity and excellent in storage stability.

The second object of the present invention is to provide a metal oxide powder coated with a dense and practical silica coating having specific characteristics and a good shape-following capability, and a method for producing the silica-coated metal oxide powder.

DISCLOSURE OF THE INVENTION

As a result of extensive investigations to achieve the first object, the present inventors have found that cosmetics having blended therein silica-coated metal oxide powder obtained by coating a metal oxide with a silica film to have a thickness of from 0.1 to 100 nm, have desired characteristics, and attained the first aspect of the present invention.

More specifically, the first aspect of the present invention relates to cosmetics comprising silica-coated metal oxide powder obtained by coating a metal oxide with a silica film to have a thickness of from 0.1 to 100 nm. Further, the present invention relates to the cosmetics above wherein the photocatalytic activity measured by the tetralin auto-oxidation method is 6 mmH$_2$O/min or less, the cosmetics above wherein the silica-coated metal oxide powder having a primary particle size of from 5 to 500 nm and a secondary particle size of from 0.5 to 10 μm, the cosmetics above wherein the silica-coated metal oxide powder has a primary particle size of 5 to 120 nm and a silica coating thickness of 0.5 to 25 nm.

Furthermore, the present invention relates to the cosmetics above wherein the metal oxide is one or more metal oxide selected from the group consisting of titania, zinc oxide, zirconium oxide, cerium oxide and iron oxide, and the cosmetics above wherein the metal oxide is titania, the cosmetics above wherein the metal oxide is zinc oxide, the cosmetics above wherein the metal oxide is cerium oxide, the cosmetics above wherein an anti-oxidant is incorporated, and the cosmetics above wherein a ultraviolet absorbent is incorporated.

To attain the above second object, the present invention provides a metal oxide powder coated with a practical and dense silica coating which is produced without passing through calcination, has specific absorption peaks in the infrared absorption spectra, exhibits high shape following capability to the complicated particle shape of the base material metal oxide and ensures good coating property even if the thickness is very small.

The term "dense" as used herein means that the silica coating formed has a high density and is uniform and free of pin holes or cracks. The term "practical" as used herein means that the bonding between the silica and the base material metal oxide (—Si—O—M bonding where M stands for a metal element such as Ti, Zn, Co, Zr and Fe) is strong, as a result, peeling or the like of the coating is not caused and the physical properties of the silica-coated metal oxide powder are not impaired.

The silica coating used in the silica-coated metal oxide powder of the present invention has an absorption peak intensity ratio I ($I=I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of 1,150 to 1,250 cm$^{-1}$ and the region of 1,000 to 1,100 cm$^{-1}$ of 0.2 or more, and a refractive index of 1.435 or more.

In other words, this is a metal oxide powder coated with a silica coating which is dense and practical, having the chemical bond or functional group as formed in the case of not using calcination in a conventional method.

The silica-coated metal oxide powder of the present invention exhibits specific physical properties with respect to hydrophilicity, absorption ability of oil or the like and the coating thereof is dense and practical.

The silica coating of the present invention is dense, therefore, it forms a strong coating and additionally exhibits advantageous effects such as high shape following capability to the complicated particle shape of the base material metal oxide, good coating properties even in the case of forming a very thin coating having a thickness of about 0.5 nm, and capability of shielding the photocatalytic activity of the metal oxide.

When the coating contains an alkali metal such as sodium, the silica coating may dissolve in a hot, high humidity atmosphere, however, in the silica coating of the present invention, the content of an alkali metal such as sodium can also be made to be very small.

In accordance with the third aspect of the present invention, the above silica-coated metal oxide powder is obtained by contacting a silica film-forming composition mainly comprising a) silicic acid, b) water, c) an alkali, d) an organic solvent, and a reaction product thereof, said composition having a silica concentration of from 0.0001 to 5 mol/l and a water/organic solvent ratio of from 0.1 to 10, preferably from 0.1 to 0.5, with a metal oxide powder and while maintaining the contact, selectively depositing the silica on the surface of the metal oxide powder. This method can dispense with calcination and is industrially useful.

BEST MODES FOR CARRYING OUT OF THE INVENTION

Figure 1:
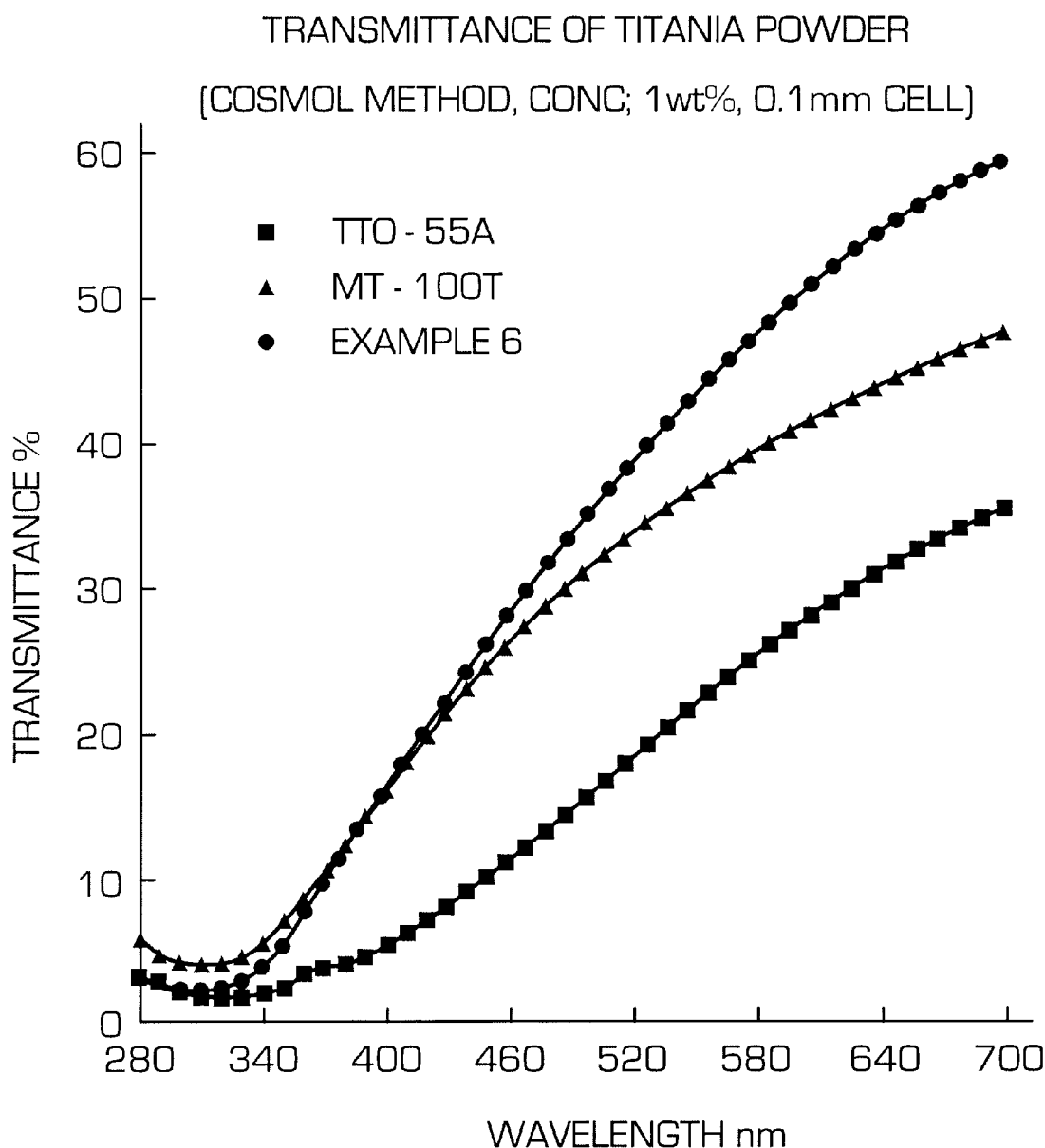
FIG. 1 shows light transmittances of a silica-coated titania powder of an Example and a conventional surface treated titania powder.

The present invention is described more in detail in the following.

The process for producing (the third aspect) a silica-coated metal oxide powder (the second aspect) which can be preferably used in cosmetics (the first aspect) in accordance with the present invention, is first described.

As the cosmetic of the present invention, a silica-coated metal oxide powder obtained by a process comprising contacting a metal oxide with a silica film-forming composition comprising silicic acid, water, alkali and an organic solvent, the composition having a water/organic solvent ratio of from 0.1 to 10 and a silicon concentration of from 0.0001 to 5 mol/l, to selectively deposit silica on the surface of the metal oxide powder, may be used.

Particularly, a silica-coated metal oxide powder coated with a silica having an absorption peak intensity ratio I ($I=I_1/I_2$, wherein $I_1$ is an absorption peak intensity at from 1,150 to 1,250 cm$^{-1}$ and $I_2$ is an absorption peak intensity at from 1,000 to 1,100 cm$^{-1}$) between the infrared absorption spectra in the region of from 1,150 to 1,250 cm$^{-1}$ and the region of from 1,000 to 1,100 cm$^{-1}$ of 0.2 or more, and having a refractive index of 1,435 or more, may be preferably used for the cosmetics of the present invention.

The silicic acid for use in the composition of the present invention includes those described, for example, in *ENCYCLOPAEDIA CHIMICA. "SILICIC ACID"*, 7th ed., Kyoritsu Shuppan KK (Mar. 15, 1969), such as orthosilicic acid $H_4SiO_4$ and as polymers thereof, metasilicic acid $H_2SiO_3$, mesosilicic acid $H_2SiO_5$, mesotrisilicic acid $H_4Si_3O_8$ and mesotetrasilicic acid $H_6Si_4O_{11}$. The silicic acid does not contain an organic group or halogen.

The composition containing a silicic acid of the present invention can be obtained, for example, by adding water, an alkali and an organic solvent to tetraalkoxysilane ($Si(OR)_4$, wherein R is a hydrocarbon group, preferably an aliphatic group having from 1 to 6 carbon atoms) as a precursor, such as tetramethoxysilane, tetraethoxysilane, tetra-n-propoxysilane, tetraisopropoxysilane and tetra-n-butoxysilane, and stirring the solution to allow the hydrolysis reaction to proceed. This method is preferred because the handling or operation is facilitated and practical. A particularly preferred material is tetraethoxysilane.

The compound having a hydrophobic group such as a hydrocarbon group, a halogen or hydrogen, represented by the formula: $X_nSi(OH)_{4-n}$ [wherein X represents a hydrocarbon group, a halogen or hydrogen and n represents an integer of 1, 2 or 3] differs from the silicic acid used in the present invention. Accordingly, trialkoxyalkylsilane, dialkoxydialkylsilane, trialkoxysilane, dialkoxysilane and the like are not suitable as the precursor.

The composition containing a silicic acid may also be obtained by a method of adding water, an alkali and an organic solvent to silane tetrahalide and hydrolyzing silane tetrahalide, a method of adding an alkali and an organic solvent to a water glass, or a method of treating a water glass with a cationic exchange resin and adding thereto an alkali and an organic solvent.

The tetraalkoxysilane, silane tetrahalide and water glass used as a starting material of the silicic acid are not particularly limited and those commonly used as an industrial grade or a reagent grade may be used, however, a material having a higher purity is preferred. The composition for forming a silica coating of the present invention may contain an unreacted material of the above-described starting material of the silicic acid.

The amount of the silicic acid is not particularly limited, however, in terms of the silicon concentration, it is preferably from 0.0001 to 5 mol/l, more preferably from 0.001 to 5 mol/l. If the silicon concentration is less than 0.0001 mol/l, the silica coating is deposited at a very low rate and this is not practical, whereas if it exceeds 5 mol/l, the coating is not formed but silica particles may be produced in the composition.

The silicon concentration may be calculated from the added amount of the raw material of the silicic acid, such as tetraethoxysilane, however, it can be determined by the atomic absorption spectrometry of the composition. The measurement is preferably performed using a spectrum of silicon at a wavelength of 251.6 nm as the analysis line and an acetylene/nitrous oxide flame.

The water for use in the silica film-forming composition is not particularly limited, however, it is preferably water from which particles are removed by filtration or the like. If particles are contained in the water, they are adversely mixed into the product as an impurity.

The water is used in an amount such that the water/organic solvent ratio by volume is from 0.1 to 10. If the amount of water used departs from this range, the coating may not be formed or the coating formation rate extremely decreases. The water/organic solvent ratio is preferably from 0.1 to 0.5. When the water/organic solvent ratio is from 0.1 to 0.5, the kind of alkali used is not limited. Outside this range, namely, when the water/organic solvent ratio is from 0.5 or more, the coating is preferably formed by using an alkali containing no alkali metal, such as ammonia, ammonium hydrogencarbon or ammonium carbonate.

The alkali for use in the composition of the present invention is not particularly limited, however, examples thereof include inorganic alkalis such as ammonia, sodium hydroxide and potassium hydroxide, inorganic alkali salts such as ammonium carbonate, ammonium hydrogencarbonate, sodium carbonate and sodium hydrogencarbonate, organic alkalis such as monomethylamine, dimethylamine, trimethylamine, monoethylamine, diethylamine, triethylamine, pyridine, aniline, chorine, tetramethylammonium hydroxide and guanidine, and organic acid alkali salts such as ammonium formate, ammonium acetate, monomethylamine formate, dimethylamine formate, pyridine lactate, guanidinoacetic acid and aniline acetate. Among these, ammonia, ammonium carbonate, ammonium hydrogencarbonate, ammonium formate, ammonium acetate, sodium carbonate and sodium hydrogencarbonate are preferred. The alkali may be used either independently or in combination of two or more thereof.

The alkali for use in the present invention is not particularly limited in its purity and a commonly used industrial grade or reagent grade may be used, but an alkali having a higher purity is preferred.

The coating formation rate can be effectively increased by elevating the coating temperature. In this case, an alkali and an organic solvent difficult to volatilize or decompose at the coating temperature are preferably used.

The coating may be formed by adding a slight amount of alkali, for example, about 0.002 mol/l of sodium carbonate, but the alkali may also be added in a large amount of about 1 mol/l. However, if a solid alkali is added in excess of its solubility, it is mixed into the metal oxide powder as an impurity and this is not preferred.

By using an alkali not containing an alkali metal as a main component, a silica-coated metal oxide powder reduced in the alkali metal content can be prepared. In view of the coating formation rate and the facilitated removal of the residual matters, ammonia, ammonium carbonate and ammonium hydrogencarbonate are preferred.

The organic solvent for use in the film-forming composition is preferably one which provides as a uniform solution. Examples thereof include alcohols such as methanol, ethanol, propanol and pentanol, ethers, acetals such as tetrahydrofuran and 1,4-dioxane, aldehydes such as acetaldehyde, ketones such as acetone, diacetone alcohol and methyl ethyl ketone, and polyhydric alcohol derivatives such as ethylene glycol, propylene glycol and diethylene glycol. Among these, alcohols are preferred, and ethanol is more preferred. These organic solvents may be used either individually or in combination of two or more thereof.

The organic solvent for use in the present invention is not particularly limited in its purity and a commonly used industrial grade or reagent grade may be used, however, an organic solvent having a higher purity is preferred.

The composition for forming a silica coating of the present invention can be prepared by a solution preparation method in general. For example, an alkali and water each in a predetermined amount are added to an organic solvent and after stirring the solution, tetraethoxysilane is added thereto and the mixture is stirred. A coating can be formed using any order of addition in the mixing. In the mixing of water and tetraethoxysilane, both are preferably diluted with an organic solvent in view of the reaction control.

The thus-prepared composition for forming a silica coating of the present invention is a stable composition and causes substantially no deposition or precipitation before the composition is brought into contact with a metal oxide powder. When a metal oxide powder is contacted with the composition, silica starts to selectively deposit on the surface of the metal oxide powder.

The metal oxide as a raw material for a silica-coated metal oxide powder is preferably one or more metal oxides selected from the group consisting of titania, zinc oxide, cerium oxide, zirconium oxide and iron oxide. The process for producing the metal oxide powder as a raw material is not particularly limited and may be any processes. For example, in the case of a titania powder, it may be one produced by any method such as high temperature gas phase oxidation of $TiCl_4$, gas phase hydrolysis of $TiCl_4$, a sulfuric acid method or a chlorine method, and may be one produced by gas phase hydrolysis of a alkoxy titanium such as tetraethoxy titanium, tetraisopropoxy titanium and tetranormalpropoxy titanium.

The crystallinity of the metal oxide may any crystal type. For example, titania may be any type of amorphous, rutil, anatase, brookite and a mixture thereof. However, the metal oxide powder has preferably little impurity and less aggregation for control of the secondary particle size.

Fundamentally, a silica coating can be formed by soaking a metal oxide powder in the silica coating-forming composition and maintaining the composition at a prescribed temperature and depositing selectively silica on the surface of the metal oxide. The method may be a method of previously preparing a coating-forming composition and then pouring a metal oxide powder therein to deposit a silica coating, or a method of previously dispersing a metal oxide powder in a solvent followed by adding other starting components to form a coating-forming composition, to thereby form a silica coating, or other method. That is, the order of adding raw materials of the coating-forming composition and a metal oxide powder is not particularly limited and a coating layer can be formed by first pouring any component.

The present inventors have found that among the above methods, when tetraalkoxysilane diluted with a solvent is added gradually on a suspension of a metal oxide powder, a solvent, water and an alkali, a silica coating having a high density can be formed and using this, an industrially useful continuous process can be constructed.

The silica coating grows with the deposition of a metal oxide and therefore, the thickness of the coating can be made larger by increasing the coating formation time. Of course, when the majority of the silicic acid in the coating-forming composition is consumed by the coating formation, the coating formation rate decreases, but by adding in sequence silicic acid corresponding to the consumed portion, a coating-formation can be continued at a practical rate.

Further, it has been also found that a continuous economical process with high productivity can be established in such a manner that, by using a silicic acid component corresponding to the amount of the silica coating, metal oxide powder is held in a coating-forming composition during a prescribed time to consume the silicic acid component and deposit a silica coating, the coating is taken out from the system as a silica-coated metal oxide powder product, subsequently a silicic acid component is added to the system and the composition is used for the formation of a coating on the next metal oxide powder.

The temperature of the composition for the deposition during the coating formation is not particularly limited, however, it is preferably from 10 to 100° C., more preferably from 20 to 50° C. As the coating formation temperature is higher, the coating formation rate more increases, however, if the coating formation temperature is too high, it becomes difficult to keep the solution composition constant due to volatilization of the components in the composition. If the temperature is too low, the coating formation rate becomes slow and it is not practical.

The pH during the coating formation may be in a range of an alkali pH. However, when a metal oxide whose solubility increases depending on the pH is coated with silica, the pH of the coating-forming composition is preferably controlled. For example, in producing a silica-coated zinc oxide, it is preferred that the pH is reduced and the pH during the coating formation is controlled to 11 or less. If the pH is above 11, the yield of a silica-coated product may decrease. Further, since the coating forming rate is reduced due to decrease in the amount of the alkali, it is preferred that a practical coating formation rate is maintained by increasing the coating-forming temperature or increasing the concentration of the silicic acid.

After the coating is formed, solid-liquid separation is performed. The separation may be performed by a general separation method such as filtration, decantation or centrifugation.

After the separation, drying is performed. The drying may be performed by a general drying method such is as natural drying, hot air drying, vacuum drying or spray drying.

The method of producing a silica-coated metal oxide powder used in the present invention does not particularly need calcinating the coating.

The silica coating obtained in the above process has an absorption peak intensity ratio $I=I_1/I_2$ (wherein $I_1$ is an absorption peak intensity in the range of from 1,150 to 1,250 $cm^{-1}$ and $I_2$ is an absorption peak intensity in the range of from 1,000 to 1,100 $cm^{-1}$) in the infrared absorption spectrum at from 1,150 to 1,250 $cm^{-1}$ and from 1,000 to 1,100 $cm^{-1}$ of 0.2 or more and a refractive index of 1.435 or more. That is, this silica coating is a dense and practically useful silica film although it has the chemical bonds and functional groups of a silica coating obtained by conventional sol-gel method without calcinating and therefore it has particular properties such as hydrophillicity and oil adsorption different from those of a silica coating obtained with calcinating. Here, the term "dense" as used means that the silica coating formed has a high density and is uniform and free of pin holes or cracks. The term "practical" as used means that the bonding between the silica and the base material metal oxide (—Si—O—M—bonding where M stands for Ti, Zn, Ce, Zr or Fe) is strong, as a result, peeling or the like of the coating is not caused and the physical properties of the silica-coated metal oxide powder are not impaired. Furthermore, the above silica coating has a good compatibility with a complicated shape of a metal oxide powder as the base material, and even if the coating thickness is as thin as 0.5 nm, the coverage is excellent and the shielding effect of photocatalytic activity is high. Also, since the silica coating can be made having an extremely low content of alkali metal, a silica-coated metal oxide powder in which the silica coating is not dissolved under a high temperature and high humidity and the physical properties of the coated powder are not altered can be obtained.

If the silica-coated metal oxide powder used in cosmetics in the present invention has a silica coating thickness of from 0.1 to 100 nm, preferably from 0.5 to 25 nm, cosmetics having sufficiently high photocatalyst shielding effect may not be obtained, whereas if it is outside this range, cosmetics having sufficiently high ultraviolet shielding ability may not be provided.

The photocatalytic activity measured by the tetralin auto-oxidation process of the silica-coated metal oxide powder used in the present invention is 6 $mmH_2O$/min or less. If it is outside this range, a sufficient effect of shielding the photocatalytic activity may not be obtained.

The silica-coated metal oxide powder obtained in the present invention preferably has a primary particle size of from 5 to 500 nm, preferably 5 to 120 nm and a secondary particle size of from 0.5 to 10 μm. If this range is not satisfied, the prepared cosmetics are liable to fail by having a poor feeling during use and low ultraviolet shielding ability at the same time. The primary particle and the secondary particle are defined in Kiichiro Kubo et al. (compiler), *Funtai (Powder)*, pp. 56–66 (1979).

The powder kinetic friction coefficient measured by glass plate method, of the silica-coated metal oxide used in the present invention, is preferably 0.54 or less, more preferably 0.49 or less. If it exceeds 0.54, cosmetics having good feeling on use may not be obtained.

The fading rate of dye measured by the Sunset Yellow method, of a silica-coated metal oxide powder used in the present invention is preferably 0.06 or less, more preferably 0.02 or less. If it exceeds 0.06, the effect of shielding photocatalytic activity may be insufficient and highly storage stable cosmetics may not be obtained.

The rate of decomposition of organic ultraviolet absorbent measured by Parsol method, of a silica-coated metal oxide powder used in the present invention, is preferably 0.02 or less, more preferably 0.01 or less. If it is less than 0.02, the effect of shielding photocatalytic activity may be insufficient and cosmetics with a lower decomposition of an organic ultraviolet absorbent may not be obtained.

In accordance with the silica-coated metal oxide powder used in the present invention, cosmetics with transparency are obtained since the coated powder has a high visible light transmittance while maintaining a high ultraviolet ray shielding effect.

The silica-coated metal oxide powder used in the present invention need not be calcined, but may be calcined, before use.

The above silica-coated metal oxide powder which has been developed for the purpose of providing cosmetics is novel and the present invention also provides such a novel silica-coated metal oxide powder.

The novel silica-coated metal oxide powder may be applied not only to cosmetics but also widely to pigment, ultraviolet shielding material and photocatalyst with a controlled activity.

The cosmetics of the present invention can be produced by incorporating the silica-coated metal oxide powder prepared as above with normal raw materials capable of blending into cosmetics according to the usual production process.

The cosmetics of the present invention are not particularly limited as long as they contain the powder but the cosmetics include solvents or solutions in which powder is dispersed, for example, powder-containing cosmetics are cosmetics in the form of a powder, press, stick or liquid, more specifically, a face powder, foundation, powder, cheek rouge, eye shadow, lipstick, eyeliner, mascara, eyebrow and so on. The cosmetics in which a powder is dispersed in a solvent or solution include, for example, cream, essence, lotion, beauty wash, milky lotion (latex), mousse and so on. Solid powder cosmetics are particularly preferred.

The solid powder cosmetic of the present invention comprises a powder part and an oil. The powder part is constituted by the silica-coated metal oxide powder of the present invention as well as an extender such as mica, talc, kaolin, calcium carbonate, magnesium carbonate, silicic acid anhydrate, aluminum oxide, and barium sulfate, a white pigment such as titanium oxide and zinc oxide and a color pigment such as red iron oxide, yellow iron oxide, black iron oxide, chromium oxide, ultramarine, Berlin blue and carbon black. These may be used in combination. Furthermore, in order to still further improve the usability, a spherical powder such as nylon powder and polymethyl methacrylate powder may also be used.

The solid powder cosmetic of the present invention contains an oil. Examples of the oil used include liquid paraffin, squalane, castor oil, glyceryl diisostearate, glyceryl triisostearate, glyceryl tri-2-ethylhexanoate, isopropyl myristate, glyceryl triisostearate, dimethyl polysiloxane, methyl phenyl polysiloxane, vaseline, diisostearyl malate and refined lanolin. The amount of oil incorporated is from 1 to 35 wt %, preferably from 10 to 25 wt %, based on the solid powder cosmetic.

In the oil, an organic ultraviolet absorbent may be blended. The organic ultraviolet absorbent means an organic compound which absorbs ultraviolet rays and convert them to heat, vibration, fluorescence, radicals and other energies to have a function of protecting skins. The ultraviolet absorbent which can be used in the cosmetics of the present invention is not limited and includes Palsol A, benzophenone-base ultraviolet absorbents, salicylic acid-base ultraviolet absorbents, PABA-base ultraviolet absorbents, cinnamate-base ultraviolet absorbents, cinnamate-base ultraviolet absorbents, dibenzoylmethane-base ultraviolet absorbents, and arocanate-base ultraviolet absorbents. The amount of the ultraviolet absorbent blended is from 0.1 to 10 wt %, however, an appropriate amount is preferably selected in the blending according to the ultraviolet absorbing ability of the absorbent. The silica-coated metal oxide powder used in the present invention can provide good ultraviolet-shielding cosmetics even of combined with an organic ultraviolet absorbent since the shielding effect of photocatalytic activity is high and decomposition of the absorbent is prevented.

The cosmetics of the present invention may contain an existing emulsifier in a general concentration. Examples of the emulsifier which can be used include those described in Kesho-hin Genrvo Kijun Dainihan Chukai (*Japanese Standards of Cosmetic Ingredients, 2nd Ed., Notes*), compiled by Nippon Koteisho Kyokai, published by Yakuji Nippo, Ltd. (1984), Kesho-hin Genryo Kijun-gai Seibun Kikaku (*Japanese Cosmetic Ingredient Codex*), supervised by Examination Division, Pharmaceutical Affairs Bureau, Ministry of Health and Welfare, published by Yakuji Nippo, Ltd. (1993), Kesho-hin Genryo Kijun-gai Seibun Kikaku, Tsuiho (*Standards for Ingredients out of Materials of Cosmetics, Supplement*), supervised by Examination Division, Pharmaceutical Affairs Bureau, Ministry of Health and Welfare, published by Yakuji Nippo, Ltd. (1993), *The Comprehensive Licensing Standards Of Cosmetics By Category*, supervised by Examination Division, Pharmaceutical Affairs Bureau, Ministry of Health and Welfare, published by Yakuji Nippo, Ltd. (1993), and Kesho-hin Genryo Jiten (*Dictionary of Raw Materials of Cosmetics*), Nikko Chemicals, Inc. 1991. Tochopheryl phosphates can be used as an emulsifier.

The cosmetics of the present invention may be used in combination or mixed with an existing anti-inflammatory or antiphlogistic ingredient so as to prevent inflammation due to ultraviolet rays. The antiphlogistic which can be added to the cosmetics of the present invention is not particularly limited and examples thereof include an aniline derivative-type antiphlogistic, a salicylic acid derivative-type antiphlogistic, a pyrazolone derivative-type antiphlogistic, and indomethacin-base antiphlogistic, mefenamic acid-base antiphlogistic, antarthritis, spasmolytic, antitussive, expectorant, bronchodilator, respiratory function improver, antihistamines, antiallergics, and anti-inflammatory enzymes.

When a substance having antioxidant ability is simultaneously added to the cosmetics of the present invention, cosmetics with reduced phototoxicity can be obtained by suppressing the amount of free radicals generated by ultraviolet rays. Examples of the antioxidants which are simultaneously added in the present invention and have an effect of suppressing the phototoxicity include vitamin A, β-carotene, astaxanthin, vitamin B, vitamin C, magnesium L-ascorbyl-2-phosphate, sodium L-ascorbyl-2-phosphate, magnesium sodium L-ascorbyl-2-phosphate, L-ascorbyl-2-glucoside, L-ascorbyl-2-phosphate-5,6-benzylidene, natural vitamin E, dl-α-tocopherol, dl-α-tocopherylacetate, sodium dl-α-tocopherylphosphate, ubiquinone and a vitamin derivative thereof, cysteine, glutathione, glutathione peroxidase, SOD, catalase, citric acid, phosphoric acid, polyphenol, catechin, tea extract, kojic extract, nucleic acid, hydroquinone and arbutin, and one or a mixture of two or more selected from these known antioxidant may be used.

The cosmetics in accordance with the present invention may incorporate components other than the above and which are usually incorporated in cosmetics or other compositions, for example, oils and fats, waxes, hydrocarbons, aliphatic acids, alcohols, polyhydraulic alcohols, sugars, esters, metal soaps, water-soluble polymers, surfactants, anti-oxidants, insecticides antiseptics, vitamins, hormones, colorants, etc.

The amount of the silica-coated metal oxide powder in a cosmetic of the present invention is preferably 1 to 50% by weight, more preferably 5 to 30% by weight, based on the cosmetic.

In general, titania higher in the rutil proportion which has a lower photocatalytic activity than an anatase proportion, is preferably used for the silica-coated titania. However, the silica-coated titania used in a cosmetic of the present invention provides a low phototoxicity irrespective of the crystal-type, since it suppress generation of free radicals by ultra-violet rays.

The cosmetics containing the silica-coated metal oxide according to the present invention not only have a high ultraviolet ray shielding ability, but also even if the metal oxide powder is incorporated in a high concentration, do not have creaky feeling or low extensity blocking, and therefore are excellent in usability. Further, the cosmetics of the present invention have a high transparency and do not result in pale coloring of cosmetic finish as the conventional titania-containing cosmetics. Moreover, since the phototoxicity by a metal oxide is sufficiently shielded, the composition is not quickly degenerated and excellent storage stability is ensured. The cosmetics can contain an organic ultraviolet ray absorbent and can has a higher ultraviolet ray shielding capability. If an anti-oxidant having an anti-oxidation property is concosmed in the cosmetics, the safety to a human body is enhanced.

The measurement of the thickness and refractive index of the silica coating in the present invention can be attained by using a silica coating formed on a silicon wafer which has been immersed in a system when a silica-coated metal oxide powder was prepared. The silica coating formed on the silica wafer is the same as the silica coating on the metal oxide powder. The refractive index of the silica coating can be measured by ellipsometer (manufactured by ULVAC; LASSER ELLIPSOMETER ESM-1A). The thickness of the coating can be measured by a step meter.

The transmission infrared absorption spectrum of a silica-coated metal oxide powder can be measured using KBr method (manufactured by Nippon Spectrum Corp., FT-IR-8000). The primary particle size of the silica-coated metal oxide powder and the layer thickness of the silica coating can be determined by transmission type electron microscope. The secondary particle size of the coated powder can be measured by laser light scattering method (manufactured by Nikkiso Corp.; Microtrack MK-II). The total content of the all alkalis is measured by dissolving the silica-coated metal oxide metal oxide powder in fluorosurfric acid and by flame photometry.

The photocatalytic activity, i.e., the initial oxygen consumption rate of a silica-coated metal oxide powder can be measured by a tetralin auto-oxidation method (Manabu Kiyono "Titanium Oxide-Physical Properties and Applied Technology, Giho-do-shuppan, p. 196–197, 1991). The initial oxygen consumption rate (mm $H_2O$/min) is measured using pure tetralin, an amount of metal oxide added of 0.1%, a pressure of oxygen of 760 mmHg, a reaction temperature of 40° C., a liquid stirring rate of 260 rpm and a mercury lamp-irradiated ultraviolet ray intensity of 350 $\mu W/cm^2$.

The light transmittance of the silica-coated metal oxide powder, the rate of decomposition of the organic ultraviolet absorbent, the powder kinetic friction coefficient and the dye fading rate are measured by Cosmol method, Parsol method, glass plate method, and sunset yellow method, respectively.

EXAMPLES

The present invention is described below by referring to the Examples, however, the present invention should not be construed as being limited thereto.

Example 1
Preparation of Silica-coated Titania Powder

Into a 5 l-volume reactor, 400 ml of de-ionized water, 1388 ml of ethanol (produced by Junsei Chemical Corp.) and 87 ml of 25% aqueous ammonia (produced Taisei Chemical Industries) were mixed, and therein, 105 g of titania powder (titania, F-1 produced by Showa Titanium KK, primary particle size: 90 nm) was dispersed to prepare Suspension 1. Next, 193 ml of tetraethoxysilane (produced by NACALAI TESQUE, INC.), 24 ml of water and 156 ml of ethanol were mixed to prepare Solution 1.

To Suspension 1 under stirring with a magnetic stirrer, Solution 1 was added at a constant rate over 6 hours, and then, the mixture was aged for 12 hours. The coating and aging were performed at 25° C. Thereafter, the precipitate was centrifuged and dried under vacuum at 50° C. for 12 hours to obtain silica-coated titania powder.

Example 2
Preparation of Silica-coated Zinc Oxide Powder

Into a 5 l-volume reactor, 991 ml of de-ionized water, 1083 ml of ethanol (produced by Junsei Chemical Corp.), and 6.7 ml of 25% aqueous ammonia (produced by Taisei Chemical Industries) were mixed, and therein, 67 g of zinc oxide powder (produced by Sumitomo Oosaka Cement, MZ0350, primary particle size: 37 nm) was dispersed, to prepare Suspension 2. Next, 135 ml of tetraethoxysilane (produced by NACALAI TESQUE INC.) and 60 ml of ethanol were mixed to prepare Solution 2.

To Suspension 2 under stirring with a stirrer, Solution 2 was added at a constant rate over 8.5 hours, and then, the mixture was aged for 12 hours. The coating and aging were performed at a pH of 10.5 and 35° C. Thereafter, the precipitate was centrifuged and dried under vacuum at 50° C. for 12 hours, to a obtain silica-coated zinc oxide powder.

Examples 3 to 5
Preparation of Silica-coated Metal Oxide Powders

Silica-coated cerium oxide powder, silica-coated zirconium oxide powder or silica-coated red oxide powder was obtained under the same production conditions except for using cerium oxide, zirconium oxide or red oxide of iron, respectively, in place of titania in Example 1.

Example 6
Preparation of Silica-coated Titania Powder

Silica-coated titania powder was prepared under the same production conditions except for using titania having a different primary particle size (titania, produced by Showa Taitanium, F-4, primary particle size: 30 nm), in place of titania in the above.

The silica coatings of the silica-coated metal oxide powders obtained in Examples 1 to 6 were measured by the KBr method and on determination of the resulting transmission infrared absorption spectrum of each of the metal oxide powders, a peak originated from the Si—O—Si stretching vibration was observed at from 1,000 to 1,200 cm$^{-1}$ but absorption originated from the C-H stretching vibration in the region of from 2,800 to 3,000 cm$^{-1}$ was not observed. Thus, the coatings formed were identified as silica.

Further, the primary particle size, secondary particle size, absorption speak ratio I of infrared absorption spectrum, refractive index of the silica coatings, photocatalytic activity by tetralin anti-oxidation method, and total alkali metal concentrations were measured. The results are summarized in Table 1.

TABLE 1

Physical properties of silica-coated metal oxide powders

| Silica-coated metal oxide powder | Primary particle size (nm) | Secondary particle size (μm) | Thickness of coating (nm) | I value | Refractory index | Photocatalytic activity mmH$_2$O/min | Alkali ppm |
|---|---|---|---|---|---|---|---|
| Example 1 | 90 | 2 | 10 | 0.5 | 1.445 | 3.8 | 3.0 |
| Example 2 | 37 | 3 | 8 | 0.5 | 1.445 | 4.1 | 3.1 |
| Example 3 | 95 | 8 | 22 | 0.4 | 1.450 | 3.8 | 2.9 |
| Example 4 | 80 | 4 | 19 | 0.4 | 1.444 | 3.4 | 3.2 |
| Example 5 | 90 | 9 | 20 | 0.4 | 1.442 | 3.2 | 2.9 |
| Example 6 | 30 | 1 | 3 | 0.5 | 1.445 | 4.9 | 3.0 |

(Measurement of light transmittance, Cosmol method)

The silica-coated titania powder in Example 6 and two conventional surface-treated titania powders (MT100T produced by Teyca Corp. and TTO-55A produced by Ishihara Industries Inc.) were measured on their light transmittance by the Cosmol method. That is, the substance to be measured was dispersed in polyglyceryl triisostearate (Cosmol 43) to prepare a 1% slurry. The slurry was charged in a quartz cell having a thickness of 0.1 mm and the light transmittance was measured by Spectrophotometer (SHIMADZU UV-160). The results are shown in FIG. 1.

The silica-coated titania powder used in the present invention had a higher shielding ability at ultraviolet region and a higher transmittance at visible ray region, in comparison with the conventional surface-treated titania powders.

(Measurement of amount of hydroxy radicals formed)

An anti-oxidant mixture comprising 5% of β-carotene, 5% of astaxanthin, 20% of magnesium L-ascorbyl-2-phosphate, 10% of sodium L-ascorbyl-2-phosphate, 10% of L-ascorbyl-2-glucoside, 10% of L-ascorbyl-2-phosphate-5, 6-benzylidene, 10% of natural vitamin E, 5% of dl-α-tocopherol, 5% of dl-α-tocopheryl acetic ester, 5% of sodium dl-α-tocopheryl phosphate, 5% of citric acid, 5% of phosphoric acid, and 5% of epigallocatechin, was prepared. Each of the silica-coated titania powder of Example 1 mixed with the above anti-oxidant mixture, the silica-coated titania of Example 1 alone, and uncoated titania powder alone, was dispersed in water in the same titania concentration (0.5%), and using DMPO as a radical trapping agent, the amount of hydroxy radical formed under light irradiation was determined by electron spin resonance method. As a result, the amount of hydroxy radical formed was lowest for the mixture of the silica-coated titania powder and the anti-oxidants, second lowest for the silica-coated titania powder alone, and highest for the uncoated titania powder.

(Measurement of rate of decomposition of organic ultra-violet ray absorbent; Parsol method)

Each of five silica-coated metal oxide powders obtained in Examples 2 to 6, five uncoated metal oxide powders respectively corresponding to the above five coated metal oxide powders, and two conventional surface-treated titania (MT100T produced by Teica Corp. and TTO-55A produced by Ishihara Industries Inc.) was measured on its rate of decomposition of organic ultraviolet absorbent by Parsol method. That is, each substance to be measured was dispersed in a solution of 4-tert-butyl-4'-methoxydibenzoylmethane (Parsol 1789) in polyethylene glycol 300 (0.045% by weight as a Parsol solution), to prepare a 1 wt % slurry. 1.5 g of the slurry was dispersed in a glass vessel and ultraviolet rays (1.65 mW/cm$^2$) were irradiated thereto. Thereafter, 1 g of the slurry was sampled, and thereto, 2 ml of isopropyl alcohol, 2 ml of hexane and 3 ml of distilled water were added successively. Parsol 1789 was extracted in the hexane phase by stirring and the absorption (at 340 nm) in the hexane phase in a light pass length of 1 mm was measured by a spectrophotometer (SHIMADZU UV-160) as time passed (three times of 0, 5 and 10 hours after the ultraviolet ray irradiation). The rate of reduction of the absorption at 340 nm ($\Delta A_{340}$/h) was determined. The results are summarized in Table 2.

All the silica-coated metal oxide powders that can be used in the present invention had the rate of 0.01 ($\Delta A_{340}$/h) or less, which was 1/100 or less of those of the uncoated metal oxide powders and 1/20 or less of those of the conventional surface-treated titania powders. The silica-coated metal oxide powders had a smaller rate of decomposition of ultraviolet absorbent than the conventional surface-treated titania powders.

TABLE 2

Comparison of rate of decomposition of ultraviolet absorbent

| Metal oxide powder | Absorption decreasing rate ($\Delta A_{340}$/h) |
|---|---|
| Silica-coated zinc oxide powder (Example 2) | 0.001 |
| Silica-coated cerium oxide powder (Example 3) | 0.003 |
| Silica-coated zirconium oxide powder (Example 4) | 0.002 |
| Silica-coated red iron oxide powder (Example 5) | 0.001 |
| Silica-coated titania powder (Example 6) | 0.001 |
| Conventional surface-treated titania powder (MT100T) | 0.028 |
| Conventional surface-treated titania powder (TT055A) | 0.021 |
| Uncoated zinc oxide powder (raw material of Example 2) | 0.176 |
| Uncoated cerium oxide powder (raw material of Example 3) | 0.193 |
| Uncoated zirconium oxide powder (raw material of Example 4) | 0.189 |
| Uncoated red iron oxide powder (raw material of Example 5) | 0.156 |
| Uncoated titania powder (raw material of Example 6) | 0.175 |

(Measurement of powder kinetic friction coefficient, glass plate method)

Each of the six silica-coated metal oxide powders obtained in Examples 1 to 6, six uncoated metal oxide powders respectively corresponding to the above coated powders, and two conventional surface-treated titania powders (MT100T produced by Teica Corp. and TTO-55A produced by Ishihara Industries Inc.) was evaluated for its powder kinetic friction coefficient by glass plate method. That is, each of the powders to be evaluated was dispersed on a 100×200 mm glass plate in an amount of 10 mg/cm$^2$. The glass plate was placed on a test table of a surface characteristic measuring apparatus (HEDON) and the kinetic friction coefficient was determined at a load of 22.2 g/cm$^2$, a moving speed of 200 mm/min and a moving distance of 20 mm. The results are shown in Table 3.

The kinetic friction coefficient of each of the silica-coated metal oxide powders used in the present invention was 0.490 or less, and those of the uncoated metal oxide powders and the conventional surface-treated titania powders were far greater than 0.550.

TABLE 3

Comparison of powder kinetic friction coefficient

| Metal oxide powder | Powdery kinetic friction coefficient |
| --- | --- |
| Silica-coated titania powder (Example 1) | 0.4408 |
| Silica-coated zinc oxide powder (Example 2) | 0.3980 |
| Silica-coated cerium oxide powder (Example 3) | 0.4203 |
| Silica-coated zirconium oxide powder (Example 4) | 0.4002 |
| Silica-coated red iron oxide powder (Example 5) | 0.4531 |
| Silica-coated titania powder (Example 6) | 0.4467 |
| Conventional surface-treated titania powder (MT100T) | 0.5460 |
| Conventional surface-treated titania powder (TT055A) | 0.5605 |
| Uncoated titania Powder (raw material of Example 1) | 0.5843 |
| Uncoated zinc oxide powder (raw material of Example 2) | 0.6810 |
| Uncoated cerium oxide powder (raw material of Example 3) | 0.6935 |
| Uncoated zirconium oxide powder (raw material of Example 4) | 0.6894 |
| Uncoated red iron oxide powder (raw material of Example 5) | 0.6956 |
| Uncoated titania powder (raw material of Example 6) | 0.6410 |

(Measurement of dye fading rate, Sunset yellow method)

Each of the four silica-coated metal oxide powders obtained in Examples 2 to 4 and 6, four uncoated metal oxide powders respectively corresponding to the above coated-powders, and two conventional surface-treated titania powders (MT100T produced by Teica Corp. and TTO-55A produced by Ishihara Industries Inc.), was evaluated for its dye fading rate by sunset yellow method. That is, sunset yellow, a dye for cosmetics, was dissolved in 98%-glycerol in a concentration of 0.02% by weight. The powder to be evaluated was dispersed in the resultant dispersant in an amount of 0.067% by weight and the dispersant was irradiated with ultraviolet rays (UV intensity of 1.65 mW/cm$^2$). The absorption of light at a wavelength of 490 nm, which is the wavelength of light of maximum absorption by the sunset yellow, was measured for a light path length of 1 mm by Spectrophotometer (SHIMADZU UV-160) along with the time passing on and the rate of decreasing the light absorption ($\Delta A_{490}/h$) was calculated. The results are shown in Table 4.

The dye fading rates of the silica-coated metal oxide powders used in the present invention were all 0.060 ($\Delta A_{490}/h$) or less, which were about 1/1000 of those of the uncoated metal oxide powders and about 1/100 of those of the conventional surface-treated titania powders and thus the dye decomposition was suppressed.

TABLE 4

Comparison of dye fading rate

| Metal oxide powder | Dye fading rate ($\Delta A_{490}/h$) |
| --- | --- |
| Silica-coated zinc oxide powder (Example 2) | 0.006 |
| Silica-coated cerium oxide powder (Example 3) | 0.013 |
| Silica-coated zirconium oxide powder (Example 4) | 0.008 |
| Silica-coated titania powder (Example 6) | 0.018 |
| Conventional surface-treated titania powder (MT100T) | 1.390 |
| Conventional surface-treated titania powder (TT055A) | 1.340 |
| Uncoated zinc oxide powder (raw material of Example 2) | 1.668 |
| Uncoated cerium oxide powder (raw material of Example 3) | 8.695 |
| Uncoated zirconium oxide powder (raw material of Example 4) | 5.300 |
| Uncoated titanium powder (raw material of Example 6) | 22.884 |

Examples 7 to 10

Foundations

Foundations having the following formulation were prepared in accordance with the usual method. The silica-coated metal oxide powder used was each of the four silica-coated metal oxide powders obtained in Examples 1 to 4.

| Formulation of the foundation: | |
| --- | --- |
| Silica coated metal oxide powder | 15.0 wt % |
| Mica | 15.0 wt % |
| Talc | 10.0 wt % |
| Zinc white | 15.0 wt % |
| Iron oxide (red) | 1.5 wt % |
| Iron oxide (yellow) | 3.5 wt % |
| Glycerol | 10.0 wt % |
| Purified water | 30.0 wt % |
| Perfume | appropriate amount |

Comparative Examples 1 to 6

Foundations

The composition as in Examples 7 to 10 was used except that in place of the silica-coated metal oxide powders, corresponding four uncoated metal oxide powders and two conventional surface-treated titania powders were used, to prepare the foundations.

The foundations of Examples 7 to 10 and Comparative Examples 1 to 6 were subjected to a sensitivity text and feeling on use was evaluated. The results are shown in Table 5. All the foundations containing the silica-coated metal oxide powders in accordance with the present invention had good feeling on use. In contrast, the foundations containing the uncoated metal oxide powder or the conventional surface-treated titania powder gave feeling on use which was less comfortable than usual one. It was recognized that there was a corelationship between the kinetic friction coefficient of the metal oxide powder and the feeling on use of the foundation.

TABLE 5

Kinetic friction coefficient of metal oxide powder and feeling on use of foundation

|  | Used metal oxide powder | Kinetic friction coefficient | Feeling on use |
|---|---|---|---|
| Example 7 | Silica-coated titania powder (Example 1) | 0.4408 | good |
| Example 8 | Silica-coated zinc oxide powder (Example 2) | 0.3980 | extremely good |
| Example 9 | Silica-coated cerium oxide powder (Example 3) | 0.4203 | good |
| Example 10 | Silica-coated zirconium oxide powder (Example 4) | 0.4002 | extremely good |
| Com. Ex. 1 | Uncoated titania powder (raw material of Example 1) | 0.5843 | bad |
| Com. Ex. 2 | Uncoated zinc oxide powder (raw material of Example 2) | 0.6810 | bad |
| Com. Ex. 3 | Uncoated cerium oxide powder (raw material of Example 3) | 0.6935 | bad |
| Com. Ex. 4 | Uncoated zirconium oxide powder (raw material of Example 4) | 0.6894 | bad |
| Com. Ex. 5 | Conventional surface-treated titania powder (MT100T) | 0.5460 | bad |
| Com. Ex. 6 | Conventional surface-treated titania powder (TT055A) | 0.5605 | usual |

Examples 11 to 13

Foundations

Foundations having the following formulation were prepared in accordance with the usual method. The silica-coated metal oxide powder used was each of the three silica-coated metal oxide powders obtained in Examples 2 to 4.

| Formulation of the foundation: | |
|---|---|
| Silica-coated titania powder produced in Example 6 | 10.0 wt % |
| Silica-coated metal oxide powder | 5.0 wt % |
| Mica | 15.0 wt % |
| Talc | 10.0 wt % |
| Zinc white | 15.0 wt % |
| Iron oxide (red) | 1.5 wt % |
| Iron oxide (yellow) | 3.5 wt % |
| Glycerol | 10.0 wt % |
| Purified water | 30.0 wt % |
| Perfume | appropriate amount |

The foundations prepared were subjected to a sensitivity test and verified to give extremely good feeling on use.

Example 14

Foundation

A foundation having the following formulation was prepared.

| Formulation of the foundation: | |
|---|---|
| Silica-coated titania powder produced in Example 6 | 15.0 wt % |
| Mica | 15.0 wt % |
| Talc | 10.0 wt % |
| Zinc white | 15.0 wt % |
| Silica-coated red iron oxide | 1.5 wt % |
| Iron oxide (yellow) | 3.5 wt % |
| Glycerol | 10.0 wt % |
| Purified water | 30.0 wt % |
| Perfume | appropriate amount |

The foundation prepared was subjected to a sensitivity test and verified to give extremely good feeling on use.

Example 15

Sunscreen Milky Lotion

Polyethylene glycol was added to purified water and after dissolving under heating, silica-coated titania powder and bee gum were added thereto, uniformly dispersed in a homomixer and kept at 70° C. (aqueous phase). Other ingredients were mixed, dissolved under heating and kept at 70° C. (oil phase). The oil phase was added to the aqueous phase and uniformly emulsion-dispersed in a homomixer. After the emulsification, the mixture was cooled to 35° C. while stirring.

| Formulation of the sunscreen milky lotion: | |
|---|---|
| Silica-coated titania powder produced in Example 6 | 7.0 wt % |
| Stearic acid | 2.0 wt % |
| Cetyl alcohol | 1.0 wt % |
| Vaseline | 5.0 wt % |
| Silicon oil | 2.0 wt % |
| Liquid paraffin | 10.0 wt % |
| Glycerol monostearate (self-emulsifying) | 1.0 wt % |
| Polyoxyethylene (25 mol) monooleate | 1.0 wt % |
| Polyethylene glycol 1500 | 5.0 wt % |
| Bee gum | 0.5 wt % |
| Purified water | 65.5 wt % |
| Perfume | appropriate amount |
| Antiseptic | appropriate amount |

The milky lotion obtained was subjected to a sensitivity test and verified to give good feeling on use.

Example 16

Cosmetics (Face Lotion)

A face lotion was prepared according to the following formulation by the usual method.

| Formulation of the cosmetics: | |
|---|---|
| Silica-coated titania powder produced in Example 6 | 3.0 wt % |
| Ethyl alcohol | 9.6 wt % |

| Formulation of the cosmetics: | |
|---|---|
| 1,3-Butylene glycol | 9.5 wt % |
| Castor oil | 4.9 wt % |
| Methylparaben | 0.2 wt % |
| Purified water | 42.8 wt % |

The above face lotion was subjected to a sensitivity test and verified to give good feeling on use.

Example 17

Face Lotion (Milky Lotion)

A milky lotion was prepared according to the following formulation by the usual method.

| Formulation of the face lotion: | |
|---|---|
| Silica-coated titania powder produced in Example 1 | 3.0 wt % |
| Avocado oil | 11.0 wt % |
| Behenyl alcohol | 0.6 wt % |
| Stearic acid | 0.4 wt % |
| Glycerol ester of fatty acid | 0.9 wt % |
| Polyoxyethylenesorbitol fatty acid ester | 1.1 wt % |
| Polyoxyethylene alkyl ether | 0.4 wt % |
| 1,3-Butylene glycol | 10.1 wt % |
| Methylparaben | 0.2 wt % |
| Perfume | 0.4 wt % |
| Purified water | 71.9 wt % |

The above face location (milky lotion) was subjected to a sensitivity test and verified to give good feeling on use.

Example 18

Face Lotion (Cream)

A cream was prepared according to the following formulation by the usual method.

| Formulation of the cream: | |
|---|---|
| Silica-coated titania powder produced in Example 1 | 7.0 wt % |
| Squalane | 11.1 wt % |
| Stearic acid | 7.8 wt % |
| Stearyl alcohol | 6.0 wt % |
| Beeswax | 1.9 wt % |
| Propylene glycol monostearate | 3.1 wt % |
| Polyoxyethylene cetyl ether | 1.1 wt % |
| 1,3-Butylene glycol | 11.9 wt % |
| Methylparaben | 0.2 wt % |
| Perfume | 0.4 wt % |
| Purified water | 49.5 wt % |

The above cream was subjected to a sensitivity test and verified to give good feeling on use.

Example 19

Face Lotion (Cream)

A cream was prepared according to the following formulation by the usual method.

| Formulation of the cream: | |
|---|---|
| Silica-coated titania powder produced in Example 1 | 7.0 wt % |
| Silica-coated zinc oxide powder produced in Example 2 | 7.0 wt % |
| Squalane | 15.2 wt % |
| Stearic acid | 7.8 wt % |
| Stearyl alcohol | 6.0 wt % |
| Beeswax | 1.9 wt % |
| Propylene glycol monostearate | 3.1 wt % |
| Polyoxyethylene cetyl ether | 1.1 wt % |
| 1,3-Butylene glycol | 11.9 wt % |
| Methylparaben | 0.2 wt % |
| Perfume | 0.4 wt % |
| Purified water | 38.4 wt % |

The above cream was subjected to a sensitivity test and verified to give good feeling on use.

Example 20

Face Lotion (Cream)

A cream was prepared according to the following formulation by the usual method.

| Formulation of the cream: | |
|---|---|
| Silica-coated titania powder produced in Example 6 | 3.0 wt % |
| Squalane | 40.0 wt % |
| Glyceryl diisostearate | 3.0 wt % |
| Oxybenzone | 3.0 wt % |
| Organo-modified montmorillonite | 1.5 wt % |
| 1,3-Butylene glycol | 5.0 wt % |
| Octyl p-methoxy cinnamate | 5.0 wt % |
| 4-tertbutyl-4'-methoxy dibenzoylmethane | 1.0 wt % |
| Methylparaben | 0.2 wt % |
| Perfume | 0.4 wt % |
| Purified water | 37.9 wt % |

The above cream was subjected to a sensitivity test and verified to give good feeling on use.

Example 21

Cosmetics (Pack)

A pack was prepared according to the following formulation by the usual method.

| Formulation of the pack: | |
|---|---|
| Silica-coated titania powder produced in Example 1 | 7.0 wt % |
| Polyvinyl alcohol | 14.5 wt % |
| Sodium carboxymethylcellulose | 4.8 wt % |
| 1,3-Butylene glycol | 2.9 wt % |
| Ethyl alcohol | 10.0 wt % |
| Methylparaben | 0.1 wt % |
| Purified water | 60.7 wt % |

The above pack was subjected to a sensitivity test and verified to give good feeling on use.

Example 22

Cosmetics (Lipstick)

A lipstick was prepared according to the following formulation by the usual method.

| Formulation of the lipstick: | |
|---|---|
| Silica-coated titania powder produced in Example 1 | 3.0 wt % |
| Castor oil | 45.3 wt % |
| Hexadecyl alcohol | 25.2 wt % |
| Lanolin | 3.9 wt % |
| Beeswax | 4.8 wt % |
| Ozokerite | 3.4 wt % |
| Candelilla wax | 6.2 wt % |
| Carnauba wax | 2.1 wt % |
| Methylparaben | 0.1 wt % |
| Red dye | 4.8 wt % |
| Perfume | 0.1 wt % |
| Purified water | 1.1 wt % |

The above pack was subjected to a sensitivity test and verified to give good feeling on use.

Examples 23 to 26
Foundations for Sensitivity Test

Foundations having the following formulation were prepared by the usual method. The test substance was either of the four silica-coated metal oxide powders obtained in Examples 1 to 4.

| Formulation of Foundation for Sensitivity Test: | |
|---|---|
| Test substance | 15.0 wt % |
| Mica | 15.0 wt % |
| Talc | 10.0 wt % |
| Zinc white | 15.0 wt % |
| Iron oxide (red) | 1.5 wt % |
| Iron oxide (yellow) | 3.5 wt % |
| Glycerol | 10.0 wt % |
| Mixed antioxidant | 3.0 wt % |
| Purified water | 27.0 wt % |
| Perfume | appropriate amount |

In the formulation, the mixed antioxidant was a mixed substance comprising 5% of β-carotene, 5% of astaxanthin, 20% of magnesium L-ascorbyl-2-phosphate, 10% of sodium L-ascorbyl-2-phosphate, 10% of L-ascorbyl-2-glucoside, 10% of L-ascorbyl-2-phosphate-5,6-dibenzylidene, 10% of natural vitamin E, 5% of dl-α-tocopherol, 5% of dl-α-tocopherylacetic ester, 5% of sodium dl-α-tocopheryl phosphate, 5% citric acid, 5% of phosphoric acid, and 5% of epigallocatechin (% based on the weight).

Comparative Examples 7 to 11
Foundation for Sensitivity Test

Foundations were prepared using the same formulation as in Examples 23 to 26 except that the test substance was each of conventional surface-treated titania powder (produced by Teyca Inc., MT100T) and uncoated metal oxide powders corresponding to Examples 1 to 4.

(Sensitivity test)

The feeling on use of each foundation obtained in Examples 23 to 26 and Comparative Examples 7 to 11 was sensorially tested by 50 women in their twenties to forties. In the test of feeling on use, very good feeling on use gained 5 points, good 3 points, normal 2 points, bad 1 point and very bad 0 point, and the evaluation was made by adding the points of 50 women according to the five-stage rating such that the total point number of from 200 to 250 is very good (++), from 150 to 200 is good (+), from 100 to 150 is normal (+−), from 50 to 100 is bad (−) and from 0 to 50 is very bad (−−)

The results are shown in Table 6. The feeling on use of the foundation containing each of the silica-coated metal oxide powders in accordance with the present invention was very good (++). Contrarily, the feeling on use of the foundation containing the conventional surface-treated coated titania powder was normal (+−). The feeling on use of the foundation containing each of the uncoated metal oxide powders was bad (−).

TABLE 6

Results of sensitivity test

| | Used metal oxide powder | Judge |
|---|---|---|
| Example 23 | Silica-coated titania powder (Example 1) | ++ |
| Example 24 | Silica-coated zinc oxide powder (Example 2) | ++ |
| Example 25 | Silica-coated cerium oxide powder (Example 3) | ++ |
| Example 26 | Silica-coated zirconium powder (Example 4) | ++ |
| Com. Ex. 7 | Conventional surface-treated titania powder (MT100T) | +− |
| Com. Ex. 8 | Uncoated titania powder (raw material of Example 1) | − |
| Com. Ex. 9 | Uncoated zinc oxide powder (raw material of Example 2) | − |
| Com. Ex. 10 | Uncoated cerium oxide powder (raw material of Example 3) | − |
| Com. Ex. 11 | Uncoated zirconium oxide powder (raw material of Example 4) | − |

Now examples of silica-coated metal oxide powders of the present invention will be described.

Example 27

In a 1,000 ml-volume reactor, 106 ml of water, 480 ml of ethanol (produced by Junsei Kagaku) and 20 ml of 29% aqueous ammonia (produced by Junsei Kagaku) were mixed, and therein 28 g of titania powder (F-1, produced by Showa Denko) was dispersed to prepare Suspension 1. Separately, 105 ml of tetraethoxysilane (produced by NACALAI TESQUE INC.), 39.5 ml of water and 65.5 ml of ethanol were mixed to prepare Solution 1.

Solution 1 was added to Suspension 1 under stirring with a magnetic stirrer, at a constant rate over 2 hours. The mixture obtained was aged for 12 hours. The coating formation and aging were performed at 20° C. Thereafter, the solution was filtered by suction and the filtrate was dried with hot air at 80° C. for 12 hours to obtain silica-coated titania powder.

The silica coating of the silica-coated titania powder obtained in Example 27 was measured on the transmission infrared absorption spectrum (FT-IR-8000, manufactured by Nippon Bunko) according to the KBr method. The measurement was performed at a silica-coated titania powder/KBr weight ratio of 1/32 in an integration number of 64 times. Absorption originated from the Si—O—Si stretching vibration was observed at from 1,000 to 1,200 $cm^{-1}$ and absorption originated of the C-H stretching vibration was not observed at from 2,800 to 3,000 $cm^{-1}$. Thus the coating formed was identified as silica.

Further, the absorption peak intensity ratio I (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.5.

The refractive index of the silica coating was measured by an ellipsometer (LASSER ELLIPSOMETER ESM-1A, manufactured by ULVAC) and found to be 1.446.

The oil absorption of the silica-coated titania powder was measured according to the method described in JIS-K5101 and found to be 1.20 ml/g.

The silica-coated titania powder was dissolved in fluorosulfuric acid and the total alkali metal concentration was measured by the flame analysis and found to be 2.8 ppm.

Example 28

In a 5 l-volume reaction vessel, 400 ml of water, 1.4 l of ethanol (produced by Junsei Kagaku) and 75 ml of 29% aqueous ammonia (produced by Junsei Kagaku) were mixed, and therein 105 g of titania powder (F-1, produced by Showa Denko) was dispersed to prepare Suspension 1. Separately, 193 ml of tetraethoxysilane (produced by NACALAI TESQUE INC.), 36 ml of water and 144 ml of ethanol were mixed to prepare Solution 1.

Solution 1 was added to Suspension 1 under stirring with a magnetic stirrer, at once over 6 hours. The mixture obtained was aged for 12 hours. The coating formation and aging were performed at 25° C. Thereafter, the mixture was subjected to centrifuge and the filtrate was vacuum dried at 50° C. for 12 hours to obtain silica-coated titania powder.

The silica coating of the silica-coated titania powder obtained in Example 28 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^{-1}$. Thus the coating formed was identified as silica.

Further, the absorption peak intensity ratio I (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.5.

The refractive index of the silica coating was measured by an ellipsometer (LASSER ELLIPSOMETER ESM-1A, manufactured by ULVAC) and found to be 1.445.

The oil absorption of the silica-coated titania powder was measured according to the method described in JIS-K5101 and found to be 1.17 ml/g.

The silica-coated titania powder was dissolved in fluorosulfuric acid and the total alkali metal concentration was measured by the flame analysis and found to be 3.0 ppm.

Figure 2:
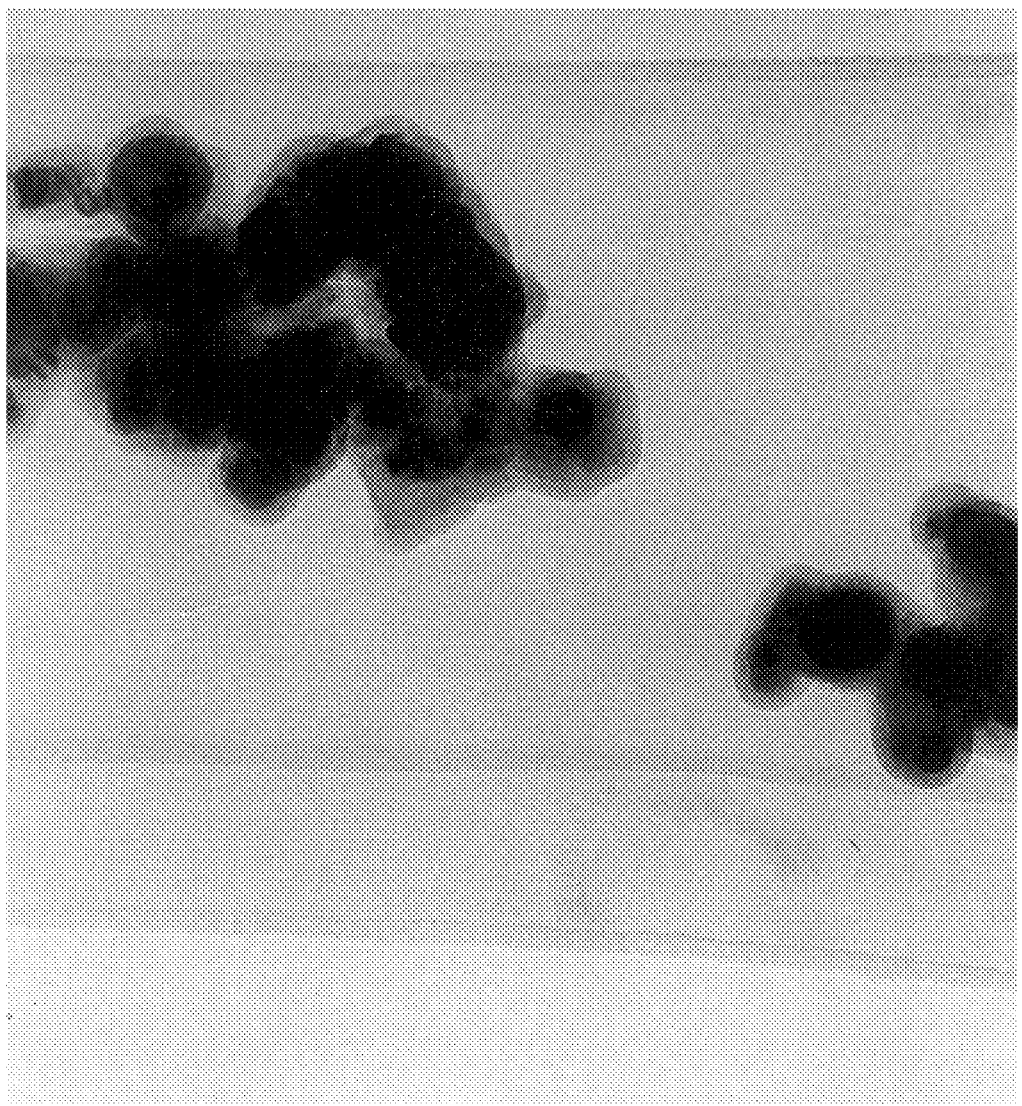
FIG. 2 is a photograph by a transmission type electron microscope of a silica-coated titania powder of an Example.

A transmission electron microscopic photograph of the silica-coated titania powder is shown in FIG. 2. It is seen that a uniform and dense coating having a good shape following capability was formed.

Example 29

In a 50 l-volume reaction vessel, 4.0 l of water, 14.0 l of ethanol (produced by Junsei Kagaku) and 750 ml of 29% aqueous ammonia (produced by Junsei Kagaku) were mixed, and therein 1.05 kg of titania powder (F-1, produced by Showa Denko) was dispersed to prepare Suspension 1. Separately, 1.93 l of tetraethoxysilane (produced by NACALAI TESQUE INC.), 360 ml of water and 1.44 l of ethanol were mixed to prepare Solution 1.

Solution 1 was added to Suspension 1 under stirring with a magnetic stirrer, at a constant rate over 6 hours. The mixture obtained was aged for 12 hours. The coating formation and aging were performed at 25° C. Thereafter, the solution was subjected to centrifuge and the filtrate was vacuum dried at 50° C. for 12 hours to obtain silica-coated titania powder.

The silica coating of the silica-coated titania powder obtained in Example 29 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^{-1}$. Thus the coating formed was identified as silica.

Further, the absorption peak intensity ratio I (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.45.

The refractive index of the silica coating was measured by an ellipsometer (LASSER ELLIPSOMETER ESM-1A, manufactured by ULVAC) and found to be 1.443.

The oil absorption of the silica-coated titania powder was measured according to the method described in JIS-K5101 and found to be 1.16 ml/g.

The silica-coated titania powder was dissolved in fluorosulfuric acid and the total alkali metal concentration was measured by the flame analysis and found to be 3.2 ppm.

Example 30

To a 5 l-volume reaction vessel, 2.27 l of a filtrate resulting from separation of the silica-coated titania powder from the finished reaction solution by the solid-liquid separation in Example 29 was added, and therein 105 g of titania powder (F-1, produced by Showa Denko) was dispersed to prepare Suspension 1. Separately, 193 ml of tetraethoxysilane (produced by NACALAI TESQUE INC.), 36 ml of water and 144 ml of ethanol were mixed to prepare Solution 1.

Solution 1 was added to Suspension 1 under stirring with a magnetic stirrer, at a constant rate over 6 hours. The mixture obtained was aged for 12 hours. The coating formation and aging were performed at 25° C. Thereafter, the solution was subjected to centrifuge and the filtrate was vacuum dried at 50° C. for 12 hours to obtain silica-coated titania powder.

The silica coating of the silica-coated titania powder obtained in Example 30 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^{-1}$. Thus the coating formed was identified as silica.

Further, the absorption peak intensity ratio I (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.45.

The refractive index of the silica coating was measured by an ellipsometer (LASSER ELLIPSOMETER ESM-1A, manufactured by ULVAC) and found to be 1.442.

The oil absorption of the silica-coated titania powder was measured according to the method described in JIS-K5101 and found to be 1.10 ml/g.

The silica-coated titania powder was dissolved in fluorosulfuric acid and the total alkali metal concentration was measured by the flame analysis and found to be 4.0 ppm.

Examples 31 to 44

Coatings were formed under the conditions shown in Table 7 in the same manner as in Example 27 by varying the kind of alkali, the water/organic solvent ratio, the kind of solvent and the silicon concentration (the amount of tetraethoxysilane), and evaluated.

TABLE 7

| Example No. | Alkali, Note[1] | Organic Solvent, Note[2] | Silicon Concentration, mol/l | Water/Organic Solvent Volume Ratio | I Value | Refractive Index | Alkali Metal Concentration, ppm |
|---|---|---|---|---|---|---|---|
| 27 | AM | ET | 0.5 | 0.25 | 0.5 | 1.446 | 2.8 |
| 31 | CN | ET | 0.5 | 0.25 | 0.3 | 1.440 | 5900 |
| 32 | PZ | ET | 0.5 | 0.25 | 0.3 | 1.439 | 3.1 |
| 33 | CN | IPA | 0.5 | 0.25 | 0.3 | 1.441 | 5400 |
| 34 | CN | THF | 0.5 | 0.25 | 0.3 | 1.442 | 5700 |
| 35 | CA | ET | 0.5 | 10 | 0.5 | 1.445 | 4.4 |
| 36 | CN | ET | 0.01 | 0.25 | 0.3 | 1.441 | 5600 |
| 37 | CN | ET | 4 | 0.25 | 0.3 | 1.442 | 5600 |
| 38 | HA | ET | 0.5 | 0.25 | 0.5 | 1.445 | 3.5 |
| 39 | PA | ET | 0.5 | 0.25 | 0.5 | 1.446 | 4.0 |
| 40 | PO | ET | 0.5 | 0.25 | 0.5 | 1.446 | 5500 |
| 41 | CA | ET | 0.5 | 0.1 | 0.3 | 1.445 | 3.6 |
| 42 | CA | ET | 0.5 | 2.5 | 0.3 | 1.443 | 3.7 |
| 43 | CN | ET | 0.5 | 0.5 | 0.4 | 1.441 | 5800 |
| 44 | CN | ET | 0.5 | 1.0 | 0.3 | 1.438 | 5900 |

Note[1]CA: ammonium hydrogencarbonate, CN: sodium hydrogencarbonate, AM: ammonia, PZ: pyridine, HA: ammonium formate, PA: ammonium acetate, PO: sodium hydroxide. All were added in an amount of 0.34 mol.
Note[2]ET: ethanol, IPA: isopropyl alcohol, THF: tetrahydrofuran.

Examples 45 to 60

Coatings were formed under the conditions shown in Table 8 in the same manner as in Example 28 by varying the kind of titania (titania different in the particle size, produced by Showa Denko) and the silicon concentration (the amount of tetraethoxysilane).

The coating formation was performed using ammonia as an alkali and ethanol as an organic solvent at a water/organic solvent ratio of 0.3. The coatings were evaluated on the transmission infrared absorption spectrum, refractive index and photocatalytic activity.

The photocatalytic activity was measured by the tetralin autoxidation method (see, Manabu Seino, Sanka Titan Bussei to Oyo Gijutu (*Titanium Oxide, Physical Properties and Applied Technology*), p. 196, Gihodo).

Example 61

A coating was formed in the same manner as in Example 28 except that tetraethoxysilane Solution 1 was added at one time.

The silica coating of the silica-coated titania powder obtained in Example 61 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^{-1}$. Thus the coating formed was identified as silica.

Further, the absorption peak intensify ratio I (I=$I_1/I_2$, wherein $I_1$ is an absorption peak intensity at 1,150 to 1,250

TABLE 8

| Example No. | Kind of Titania | Titania Primary Particle Size, nm | Silicon Concentration, mol/l | Thickness, nm | Photocatalytic Activity*, mmH$_2$O/min | I Value | Refractive Index |
|---|---|---|---|---|---|---|---|
| 28 | F1 | 90 | 0.300 | 10 | 3.7 | 0.5 | 1.445 |
| 45 | F1 | 90 | 0.140 | 5 | 3.7 | 0.5 | 1.440 |
| 46 | F1 | 90 | 0.045 | 1.25 | 3.9 | 0.4 | 1.442 |
| 47 | F4 | 30 | 0.600 | 18 | 4.0 | 0.45 | 1.441 |
| 48 | F4 | 30 | 0.300 | 4.5 | 4.9 | 0.5 | 1.445 |
| 49 | F4 | 30 | 0.140 | 2 | 3.9 | 0.4 | 1.443 |
| 50 | F4 | 30 | 0.045 | 0.5 | 5.5 | 0.35 | 1.440 |
| 51 | F6 | 20 | 3.000 | 45.0 | 3.3 | 0.4 | 1.443 |
| 52 | F6 | 20 | 0.600 | 9.2 | 3.6 | 0.4 | 1.441 |
| 53 | F6 | 20 | 0.300 | 2.3 | 3.7 | 0.5 | 1.444 |
| 54 | F6 | 20 | 0.140 | 1 | 4.3 | 0.4 | 1.442 |
| 55 | F6 | 20 | 0.045 | 0.25 | 6.6 | 0.35 | 1.439 |
| 56 | G2 | 300 | 0.600 | 304 | 3.8 | 0.35 | 1.439 |
| 57 | G2 | 300 | 0.300 | 76 | 4.3 | 0.45 | 1.444 |
| 58 | G2 | 300 | 0.140 | 33 | 3.9 | 0.5 | 1.445 |
| 59 | G2 | 300 | 0.045 | 8.25 | 3.3 | 0.4 | 1.442 |
| 60 | G2 | 300 | 0.002 | 0.37 | 4.8 | 0.35 | 1.440 |

*Only with tetralin (silica-coated titania was not added), the photocatalytic activity is 7.0 mmH$_2$O/min.

cm$^{-1}$ and I$_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.5.

The refractive index of the silica coating was measured by an ellipsometer (LASSER ELLIPSOMETER ESM-1A, manufactured by ULVAC) and found to be 1.439.

The silica-coated titania powder was measured on the photocatalytic activity by the tetralin autoxidation method and the photocatalytic activity was 6.3 mmH$_2$O/min.

The oil absorption of the silica-coated titania powder was measured according to the method described in JIS-K5101 and found to be 1.02 ml/g.

Example 62

A coating was formed in the same manner as in Example 27 and the silica-coated titania powder obtained was calcined by varying the calcination temperature.

The silica coatings of silica-coated titania powders different in the calcination conditions obtained in Example 62 were measured on the transmission infrared absorption spectrum (FT-IR-8000, manufactured by Nippon Bunko) according to the KBr method.

The absorption peak intensity ratio I (I=I$_1$I/2, wherein I$_1$ is an absorption peak intensity at 1,150 to 1,250 cm$^{-1}$ and I$_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was changed by the calcination. As the calcination temperature increased, the I value was reduced. The change in the I value is shown in Table 9.

TABLE 9

|  | Calcination Temperature | Calcination Time | I Value |
| --- | --- | --- | --- |
| 1) | not calcined | none | 0.5 |
| 2) | 200° C. | 4 hr | 0.40 |
| 3) | 400° C. | 4 hr | 0.35 |
| 4) | 600° C. | 4 hr | 0.19 |
| 5) | 900° C. | 4 hr | 0.13 |

Example 63

A coating was formed in the same manner as in Example 27 except for using tetra-n-propoxysilane (produced by Aldrich) in place of tetraethoxysilane.

The silica coating of the silica-coated titania powder obtained in Example 63 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^{-1}$. Thus the coating formed was identified as silica.

Further, the absorption peak intensity ratio I (I=I$_1$/I$_2$, wherein I$_1$ is an absorption peak intensity at 1,150 to 1,250 cm$^{-1}$ and I$_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.5.

The refractive index of the silica coating was measured by an ellipsometer (LASSER ELLIPSOMETER ESM-1A, manufactured by ULVAC) and found to be 1.443.

The oil absorption of the silica-coated titania powder was measured according to the method described in JIS-KS101 and found to be 1.20 ml/g.

Example 64

A coating was formed in the same manner as in Example 31 except that the coating formation temperature was 70° C.

The silica coating of the silica-coated titania powder obtained in Example 64 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm. Thus the coating formed was identified as silica.

Further, the absorption peak intensity ratio I (I=I$_1$/I$_2$, wherein I$_1$, is an absorption peak intensity at 1,150 to 1,250 cm$^{-1}$ and I$_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.3.

The refractive index of the silica coating was measured by an ellipsometer (LASSER ELLIPSOMETER ESM-1A, manufactured by ULVAC) and found to be 1.448.

The oil absorption of the silica-coated titania powder was measured according to the method described in JIS-K5101 and found to be 1.10 ml/g.

Comparative Example 12

The oil absorption of a titania powder (F-1, produced by Showa Denko) was measured in the same manner as in Example 27 and found to be 0.4 ml/g.

Comparative Example 13

A silica coating was formed on a silicon wafer by a general sol-gel method and the refractive index thereof was measured.

In a 1,000 ml-volume reactor, 250 g of tetraethoxysilane (produced by NACALAI TESQUE INC.), 376 g of ethanol (produced by Junsei Kagaku), 235 ml of water and 3 g of hydrochloric acid (produced by Junsei Kagaku) were added and mixed under stirring to prepare a composition solution for forming a sol-gel process coating. A silicon wafer was dipped in the solution obtained and after forming a coating at 25° C., the silicon wafer was pulled up and dried with hot air at 80° C. to obtain a sol-gel process silica coating. The refractive index was measured and found to be 1.428.

Comparative Example 14

A commercially available silica-coated titania powder (TISORB-UF 01, produced by TIOXIDE) was measured on the infrared absorption spectrum in the same manner as in Example 27 and then, the I value was 0.1. The oil absorption was 1.00 ml/g and the alkali metal concentration was 6,400 ppm.

Example 65

In a 5 l-volume reactor, 754 ml of water, 1665 ml of ethanol (produced by Junsei Kagaku) and 33 ml of 25% aqueous ammonia (produced by Junsei Kagaku) were mixed, and therein 67 g of zinc oxide powder (Mz0350, produced by Sumitomo Osaka Cement) was dispersed to prepare Suspension A. Separately, 135 ml of tetraethoxysilane (produced by NACALAI TESQUE INC.), and 75 ml of ethanol were mixed to prepare Solution B.

Solution B was added to Suspension A under stirring with a magnetic stirrer, at a constant rate over 6 hours. The mixture obtained was aged for 12 hours. The coating formation and aging were performed at pH of 10.9 and 35° C. Thereafter, the solution was centrifuged and the filtrate was dried under vacuum at 50° C. for 12 hours to obtain silica-coated zinc oxide powder.

The silica coating of the silica-coated zinc oxide powder obtained in Example 65 was measured on the transmission infrared absorption spectrum (FT-IR-8000, manufactured by Nippon Bunko) according to the KBr method. As a result, absorption originated from the Si—O—Si stretching vibration was observed at from 1,000 to 1,200 cm$^{-1}$ and absorption originated of the C-H stretching vibration was not observed at from 2,800 to 3,000 cm$^-$. Thus the coating formed was identified as silica. Further, the absorption peak intensity ratio I (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) between the infrared absorption spectra in the region of from 1,150 to 1,250 cm$^{-1}$ and the region of from 1,000 to 1,100 cm$^{-1}$ was 0.5. The refractive index of the silica coating was measured by an ellipsometer (LASSER ELLIPSOMETER ESM-1R, manufactured by ULVAC) and found to be 1.446. The oil absorption of the silica-coated zinc oxide powder was measured according to the method described in JIS-K5101 and found to be 1.19 ml/g. The silica-coated zinc oxide powder was dissolved in fluorosulfuric acid and the total alkali metal concentration was measured by the flame analysis and found to be 3.1 ppm.

TABLE 10

| pH of solution | Concentration of dissolved Zn ions (ppm) | |
|---|---|---|
| | Example 65 | Zinc oxide powder |
| 0.8 | 99 | 1,290 |
| 2.5 | 11 | 100 |
| 11.7 | 1.5 | 27 |
| 12.2 | 200 | 2,290 |
| 13.0 | 1360 | 13,480 |

Examples 66 to 73

Silica-coated zinc oxide powders were prepared by changing the type of the alkali and the kind of the solvent but the other conditions were the same as those of Example 65. The transmittance infrared absorption spectrum and refractive index were evaluated.

The coating formation conditions and the results of the evaluation are shown in Table 11.

TABLE 11

| Example No. | Alkali, Note[1] | Organic Solvent, Note[2] | Silicon Concentration, mol/l | Water/Organic Solvent Volume Ratio | I Value | Refractive Index | Alkali Metal Concentration, ppm |
|---|---|---|---|---|---|---|---|
| 65 | AM | ET | 0.23 | 0.4 | 0.5 | 1.446 | 3.1 |
| 66 | AM | IPA | 0.23 | 0.4 | 0.4 | 1.442 | 2.9 |
| 67 | AM | THF | 0.23 | 0.4 | 0.4 | 1.441 | 3.3 |
| 68 | PZ | ET | 0.23 | 0.4 | 0.5 | 1.450 | 3.2 |
| 69 | CA | ET | 0.23 | 0.4 | 0.5 | 1.444 | 4.2 |
| 70 | CN | ET | 0.23 | 0.4 | 0.4 | 1.450 | 5600 |
| 71 | HA | ET | 0.23 | 0.4 | 0.3 | 1.442 | 3.8 |
| 72 | PA | ET | 0.23 | 0.4 | 0.5 | 1.446 | 4.5 |
| 73 | PO | ET | 0.23 | 0.4 | 0.5 | 1.447 | 5800 |

Note[1]AM: ammonia, CN: sodium hydrogencarbonate, CA: ammonium hydrogencarbonate, PZ: pyridine, HA: ammonium formate, PA: ammonium acetate, PO: sodium hydroxide. All were added in an amount of 0.49 mol.
Note[2]ET: ethanol, IPA: isopropyl alcohol, THF: tetrahydrofuran.

The silica-coated zinc oxide powders prepared in Example 65 was dispersed in solutions different in pH to a concentration of 5%. After the solution was allowed to stand at 25° C. for 24 hours, the concentration of dissolved Zn ions was analyzed. The comparison was made using the zinc oxide powder prior to the silica coating. The results are shown in Table 10. The dissolution of Zn ions from the silica-coated zinc oxide powder was reduced to 1/10 or less and the resistance against acid and alkali was improved.

Examples 74 to 78

Coatings were formed under the same conditions as in Example 65 except that the amount of the alkali added was changed to vary the pH. After the coating formation, the rate of recovering the solid was determined, and the transmission infrared absorption spectrum and refractive index of the coated zinc oxide were evaluated. The results are shown in Table 2. When the pH during coating formation was beyond 11, the solid recovery rate decreased.

TABLE 12

| Example No. | Silicon Concentration, mol/l | Water/Organic Solvent Volume Ratio | Solid pH | recovery rate (%) | I Value | Refractive Index |
|---|---|---|---|---|---|---|
| 75 | 0.23 | 0.67 | 10.5 | 97 | 0.5 | 1.450 |
| 74 | 0.23 | 0.5 | 10.7 | 98 | 0.5 | 1.447 |
| 65 | 0.23 | 0.4 | 10.9 | 98 | 0.5 | 1.446 |
| 76 | 0.23 | 0.34 | 11.2 | 92 | 0.5 | 1.444 |
| 77 | 0.23 | 0.25 | 11.7 | 76 | 0.5 | 1.445 |
| 78 | 0.23 | 0.20 | 12.0 | 65 | 0.5 | 1.442 |

Examples 79 to 84

Coatings were formed under the same conditions as in Example 65 except for varying the silicon concentration. The transmission infrared absorption spectrum, refractive index and photocatalytic activity were evaluated. The results are shown in Table 13.

TABLE 13

| Example No. | Primary Particle Size, μm | Silicon Concentration, mol/l | Thickness, nm | Photocatalytic Activity*, $\Delta A_{490}$/min | I value | Refractive Index |
|---|---|---|---|---|---|---|
| 79 | 35 | 0.05 | 0.5 | 0.0004 | 0.3 | 1.438 |
| 80 | 35 | 0.14 | 2 | 0.0002 | 0.4 | 1.442 |
| 65 | 35 | 0.23 | 3 | 0.0001 | 0.5 | 1.446 |
| 81 | 35 | 0.60 | 16 | 0.0001 | 0.4 | 1.448 |
| 82 | 35 | 3.00 | 80 | 0.0001 | 0.5 | 1.450 |
| 83 | 100 | 0.05 | 1.5 | 0.0002 | 0.3 | 1.440 |
| 84 | 100 | 0.30 | 9 | 0.0001 | 0.4 | 1.439 |

The photocatalytic activity was measured by the sunset yellow method. A dye (sunset yellow) was dispersed in 98%-glycerol to a concentration of 0.02%, zinc oxide powder was added to 0.067%, and mercury lamp irradiation was made at an oxygen pressure of 760 mmHg, a reaction temperature of 40° C., a stirring rate of 260 rpm and a ultraviolet intensity of 350 $\mu$W/cm$^2$ for 60 minutes. The absorption of 490 nm wavelength light was determined while the time passed and an average absorption decreasing rate ($\Delta A_{490}$/min) was calculated. The photocatalytic activity measured as the fading rate of a dye used in a cosmetic was 0.0278 ($\Delta A_{490}$/min) for the raw material zinc oxide uncoated with silica but the silica-coated zinc oxide powder hardly exhibited photocatalytic activity.

Examples 85 to 87

Silica-coated metal oxides were prepared in the same manner as in Example 28 except that cerium oxide powder, zirconium oxide powder and red iron oxide powder were used in place of titania powder.

Examples 88 to 99

Silica-coated metal oxide powders were prepared under the same conditions as shown in Table 14 by varying the kind of alkali and the kind of solvent.

On the silica-coated metal oxide powders of Examples 85 to 99, the transmission infrared absorption spectrum and refractive index were evaluated. The coating forming conditions and evaluation results are shown in Table 14.

TABLE 14

| Example No. | Oxide Note[1] | Alkali, Note[2] | Organic Solvent, Note[3] | Silicon Concentration, mol/l | Water/Organic Solvent Volume Ratio | I Value | Refractive Index |
|---|---|---|---|---|---|---|---|
| 85 | Ce | AM | ET | 0.3 | 0.3 | 0.5 | 1.446 |
| 86 | Zr | AM | ET | 0.3 | 0.3 | 0.4 | 1.443 |
| 87 | Fe | AM | ET | 0.3 | 0.3 | 0.4 | 1.446 |
| 88 | Ce | AM | IPA | 0.3 | 0.3 | 0.4 | 1.440 |
| 89 | Ce | AM | THF | 0.3 | 0.3 | 0.4 | 1.443 |
| 90 | Ce | PZ | Et | 0.3 | 0.3 | 0.5 | 1.450 |
| 91 | Ce | CA | ET | 0.3 | 0.3 | 0.5 | 1.447 |
| 92 | Ce | CN | ET | 0.3 | 0.3 | 0.4 | 1.439 |
| 93 | Ce | HA | ET | 0.3 | 0.3 | 0.3 | 1.438 |
| 94 | Ce | PA | ET | 0.3 | 0.3 | 0.3 | 1.446 |
| 95 | Ce | PO | ET | 0.3 | 0.3 | 0.3 | 1.442 |
| 96 | Zr | AM | IPA | 0.3 | 0.3 | 0.4 | 1.441 |

TABLE 14-continued

| Example No. | Oxide Note[1] | Alkali, Note[2] | Organic Solvent, Note[3] | Silicon Concentration, mol/l | Water/Organic Solvent Volume Ratio | I Value | Refractive Index |
|---|---|---|---|---|---|---|---|
| 97 | Zr | AM | THF | 0.3 | 0.3 | 0.4 | 1.444 |
| 98 | Fe | CA | ET | 0.3 | 0.3 | 0.3 | 1.441 |
| 99 | Fe | CN | ET | 0.3 | 0.3 | 0.4 | 1.440 |

Note[1]Ce: cerium oxide, Zr: zirconium oxide, Fe: red iron oxide
Note[2]AM: ammonia, CN: sodium hydrogencarbonate, CA: ammonium hydrogencarbonate, PZ: pyridine, HA: ammonium formate, PA: ammonium acetate, PO: sodium hydroxide
all were added in an amount of 1.3 mol
Note[3]ET: ethanol, IPA: isopropanol, THF: tetrahydrofuran

We claim:

1. A cosmetic comprising a metal oxide powder coated with a dense silica coating having a thickness of from 0.1 to 100 nm and a refractive index of 1.435 or more.

2. A cosmetics as claimed in claim 1, comprising the silica-coated metal oxide powder having the photocatalytic activity determined by the tetralin auto-oxidation method of 6 mmH$_2$O/min or less.

3. A cosmetics as claimed in claim 1, wherein the silica-coated metal oxide powder has a primary particle size of from 5 to 500 nm and a secondary particle size of from 0.5 to 10 μm.

4. A cosmetics as claimed in claim 1, wherein the silica-coated metal oxide powder has a primary particle size of from 5 to 120 nm and a thickness of the silica coating of from 0.5 to 25 nm.

5. A cosmetics as claimed in claim 1, wherein the metal oxide is one or more metal oxide selected from the group consisting of titania, zinc oxide, cerium oxide, zirconium oxide and iron oxide.

6. A cosmetics as claimed in claim 5, wherein the metal oxide is titania.

7. A cosmetics as claimed in claim 5, wherein the metal oxide is zinc oxide.

8. A cosmetics as claimed in claim 5, wherein the metal oxide is cerium oxide.

9. A cosmetics as claimed in claim 1, which contains an antioxidant in addition to the silica-coated metal oxide powder.

10. A cosmetics as claimed in claim 1, which contains an organic ultraviolet absorbent in addition to the silica-coated metal oxide powder.

11. A silica-coated metal oxide powder as claimed in claim 1, having an absorption peak intensity ratio of I of said silica coating where I=I$_1$/I$_2$, wherein I$_1$ is an absorption peak intensity at from 1,150 to 1,250 cm$^{-1}$ and I$_2$ is an absorption peak intensity at from 1,000 to 1,100 cm$^{-1}$ between the infrared absorption spectra in the region of from 1,150 to 1,250 cm$^{-1}$ and the region of from 1,000 to 1,100 cm$^{-1}$ of 0.2 or more.

12. A silica-coated metal oxide powder as claimed in claim 11, wherein the metal oxide has an average particle size of from 5 to 500 nm.

13. A method for producing a silica-coated metal oxide powder, comprising contacting a metal oxide powder with a composition for forming a silica coating, said composition comprising a) silicic acid having no organic group or a precursor which can produce said silicic acid,
b) water,
c) an alkali, and
d) an organic solvent, with a water/organic solvent ratio of from 0.1 to 10 and a silicon concentration of from 0.0001 to 5 mol/l whereby due to said contacting, silica is selectively deposited on the surface of the metal oxide powder; and drying to form a metal oxide powder coated with a dense silica coating having a refractive index of 1.435 or more.

14. A method for producing a silica-coated metal oxide powder as claimed in claim 13, wherein the alkali is at least one selected from ammonia, ammonium carbonate, ammonium hydrogencarbonate, ammonium formate and ammonium acetate.

15. A method for producing a silica-coated metal oxide powder as claimed in claim 13, wherein the organic solvent is at least one selected from methanol, ethanol, propanol, pentanol, tetrahydrofuran, 1,4-dioxane and acetone.

16. A method for producing a silica-coated metal oxide powder as in claim 13, whereby said method comprises the steps of preparing a dispersion containing a metal oxide powder, water, alkali and an organic solvent, and gradually adding a mixed solution containing said silicic acid or said precursor diluted with an organic solvent and optionally water, to conduct said selective deposition of the silica on the surface of the metal oxide powder.

17. A method for producing a silica-coated metal oxide powder as in claim 13, wherein said method comprises the steps of preparing a dispersion containing a metal oxide powder, water, alkali and an organic solvent, and gradually adding a mixed solution containing said silicic acid or said precursor diluted with an organic solvent and optionally water, to conduct said selective deposition of the silica on the surface of the metal oxide powder.

18. A silica-coated metal oxide powder comprising a metal oxide powder coated with a dense silica coating having a thickness of from 0.1 to 100 nm and a refractive index of 1.435 or more.

19. A silica-coated metal oxide powder as claimed in claim 18, wherein said silica-coated metal oxide powder has a photocatalytic activity measured by tetralin anti-oxidation method of 6 mm$_{H2O}$/min or less.

20. A silica-coated metal oxide powder as claimed in claim 18, wherein said silica-coated metal oxide powder has a powder kinetic friction coefficient by glass plate method of 0.49 or less.

21. A silica-coated metal oxide powder as claimed in claim 18, wherein said silica-coated metal oxide powder has a rate of decomposition of organic UV absorber measured by Parasol method $\Delta A_{340}$/h of 0.01 or less.

22. A cosmetic as claimed in claim 1, wherein in that said silica-coated metal oxide powder has a dye fading rate by the sunset yellow method of 0.06 $\Delta A_{490}$/h or less.

23. A cosmetic as claimed in claim 1, wherein said silica-coated metal oxide powder has an absorption peak intensity ratio I of said silica coating where I=I$_1$/I$_2$, wherein $I_1$ is an absorption peak intensity at from 1,150 to 1,250 cm$^{-1}$ and $I_2$ is an absorption peak intensity at from 1,000 to 1,100 cm$^{-1}$, between the infrared absorption spectra in the region of from 1,150 to 1,250 cm$^{-1}$ and the region of from 1,000 to 1,100 cm$^{-1}$ of 0.2 or more.

24. A cosmetic as claimed in claim 1, wherein said silica-coated metal oxide powder has a powder kinetic friction coefficient by glass plate method of 0.49 or less.

25. A cosmetic as claimed in claim 1, wherein said silica-coated metal oxide powder has a rate of decomposition of organic UV absorber measured by Parasol method $\Delta A_{340}/h$ of 0.01 or less.

* * * * *